US008144891B2

(12) United States Patent
Her et al.

(10) Patent No.: US 8,144,891 B2
(45) Date of Patent: Mar. 27, 2012

(54) EARPHONE SET

(75) Inventors: Hong-Ching Her, Taichung (TW); Hung-Yue Chang, Taichung (TW); Ton-Kun Ho, Taichung (TW)

(73) Assignee: Merry Electronics Co., Ltd, Taichung (TW)

(*) Notice: Subject to any disclaimer, the term of this patent is extended or adjusted under 35 U.S.C. 154(b) by 1078 days.

(21) Appl. No.: 12/023,207

(22) Filed: Jan. 31, 2008

(65) Prior Publication Data

US 2009/0196454 A1 Aug. 6, 2009

(51) Int. Cl.
*H04R 1/10* (2006.01)
*A61F 11/06* (2006.01)

(52) U.S. Cl. .......... 381/74; 381/71.1; 381/71.6; 381/72; 381/151; 381/309; 381/312; 381/315; 381/317; 381/322; 381/324; 381/326; 381/328; 455/41.2; 455/100; 600/25; 600/300; 600/301; 607/56; 607/57

(58) Field of Classification Search .................. 381/151, 381/312, 315, 324, 326, 328, 74, 309, 317, 381/71.1, 71.6, 72; 382/322; 600/25, 300, 600/301; 607/56, 57; 455/41.2, 100
See application file for complete search history.

(56) References Cited

U.S. PATENT DOCUMENTS 6,567,524 B1 * 5/2003 Svean et al. .................. 381/71.1
6,661,901 B1 * 12/2003 Svean et al. .................. 381/328
2005/0181826 A1 * 8/2005 Yueh .......................... 455/556.2

* cited by examiner

*Primary Examiner* — Long Tran
(74) *Attorney, Agent, or Firm* — Browdy and Neimark, PLLC

(57) ABSTRACT

An earphone set includes a main device having a digital signal processor, and an earplug has an external microphone and a speaker electrically connected with the digital signal processor respectively. The external microphone converts an external sound wave into an electronic signal and transmits the electronic signal to the digital signal processor for processing. The speaker converts the electronic signal processed by the digital signal processor into a sound wave for output.

6 Claims, 7 Drawing Sheets

EARPHONE SET

BACKGROUND OF THE INVENTION

1. Field of the Invention

The present invention relates to an earphone set, and more particularly, to an earphone set with a hearing aid function that uses a digital signal processor to process electronic signals being converted from the external sound wave, thereby improving the sound quality.

2. Description of the Related Art

A hearing aid is an electroacoustic body-worn apparatus basically includes a microphone for receiving sound wave, an amplifier for amplifying the sound wave, and a combination of earphone and ear-mold for outputting sounds to the wearer's ear drum. Further, the amplifier allows the user to adjust the volume of the sound.

For a hearing-impaired, the use of a hearing aid is to amplify conversation sounds. However, the sound spectrum of surrounding noises may be overlapped with the sound spectrum of conversation sounds. In this case, the hearing aid amplifies the surrounding noises while amplifying the conversation sounds, and the wearer may be unable to distinguish the conversation sounds from the noises. The interference of surrounding noises will make the hearing-impaired to feel uncomfortable.

Further, the hearing aid has a certain dimension and must be partially inserted into the wearer's ear canal to occupy a part of the space of the ear canal. Certain ear-mold of hearing aids covers the whole ear canal so that the ear of the hearing-impaired has no room to wear an extra earphone for hearing music or radio program.

Due to wear a hearing aid, the hearing-impaired cannot wear an extra earphone on his ears, and the conventional hearing aids cannot eliminate the interference of surrounding noises for providing a high quality of sound, therefore, it is desirable to provide an earphone set that eliminates the aforesaid problems.

SUMMARY OF THE INVENTION

The present invention has been accomplished under the circumstances in view.

It is an objective of the present invention to provide an earphone set which has the function of an earphone set as well as the function of a hearing aid to be convenient for a hearing-impaired.

It is another objective of the present invention to provide an earphone which has the function of active noise cancellation for improving the sound quality.

To achieve the aforesaid objectives, the earphone set comprises a main device and at least one earplug. The main device comprises a digital signal processor for processing electronic signals. The earplug comprises an external microphone and a speaker respectively and electrically connected to the digital signal processor. The external microphone converts an external sound wave into an electronic signal and transmits the electronic signal to the digital signal processor for processing. The speaker converts the electronic signal processed by the digital signal processor into a sound wave for output.

It is still another objective of the present invention to provide an earphone set that converts the sound wave from the ear canal of a user into an electronic signal for output to a mobile phone.

To achieve this objective of the present invention, the earphone set comprises a main device and at least one earplug. The main device comprises a digital signal processor for processing electronic signals. The earplug comprises an external microphone, an internal microphone and a speaker, respectively and electrically connected to the digital signal processor. The external microphone receives an external sound wave and converts the external sound wave into an electronic signal, and then transmits the electronic signal to the digital signal processor for processing. The internal microphone receives a sound wave transmitted from the ear canal of the user who is speaking and converts the sound wave into an electronic signal, and then transmits the electronic signal to the digital signal processor for processing. The digital signal processor selectively receives the electronic signals from the external microphone and the electronic signal from the internal microphone and processes the received electronic signals for output to the speaker for converting into a sound wave.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWING

The present invention will become more fully understood from the detailed description given herein below and the accompanying drawings which are given by way of illustration only, and thus are not limitative of the present invention, and wherein.

DETAILED DESCRIPTION OF THE INVENTION

Figure 1:
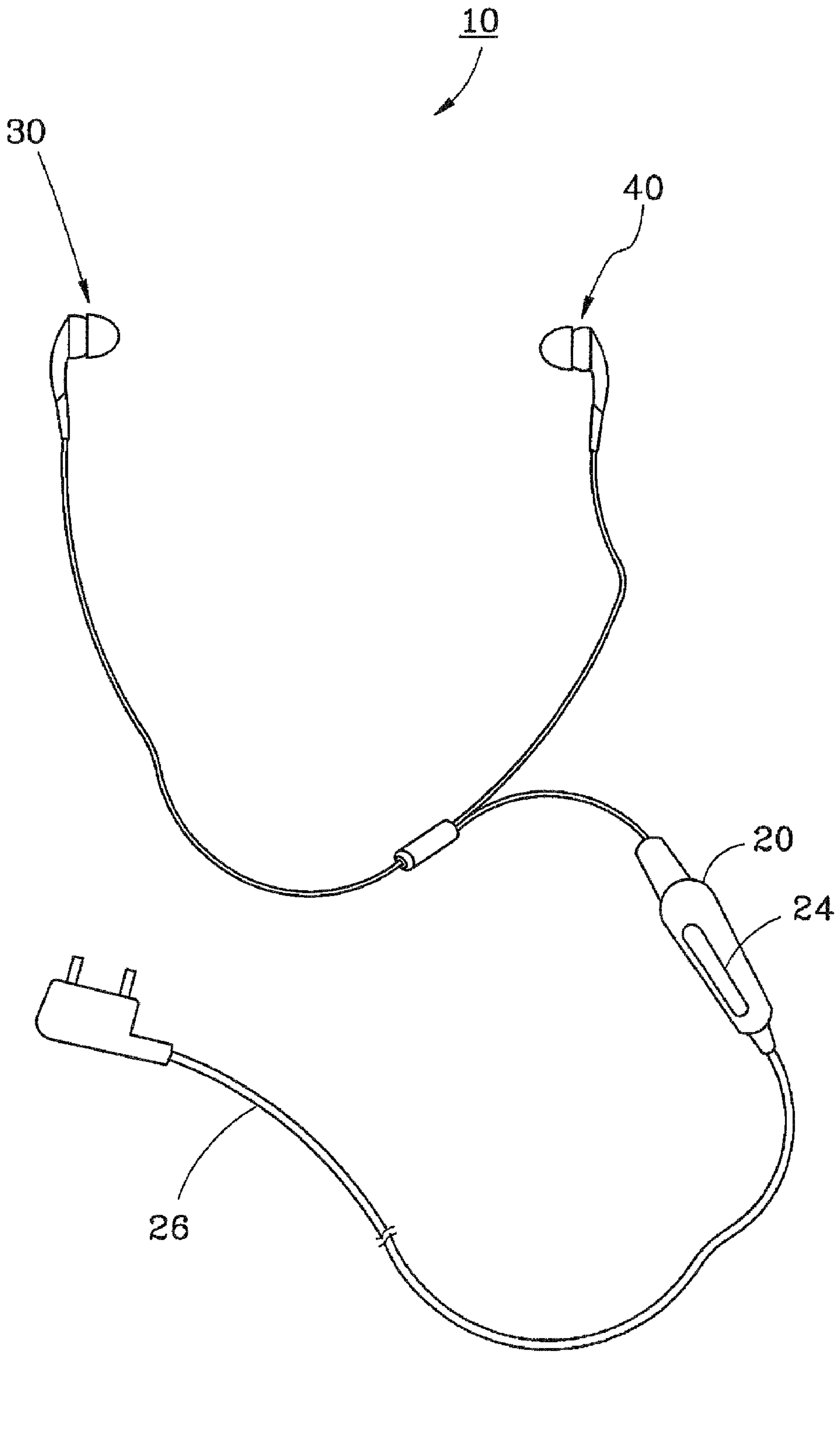
FIG. 1 is a perspective view of an earphone set in accordance with an exemplary embodiment of the present invention.
Figure 2:
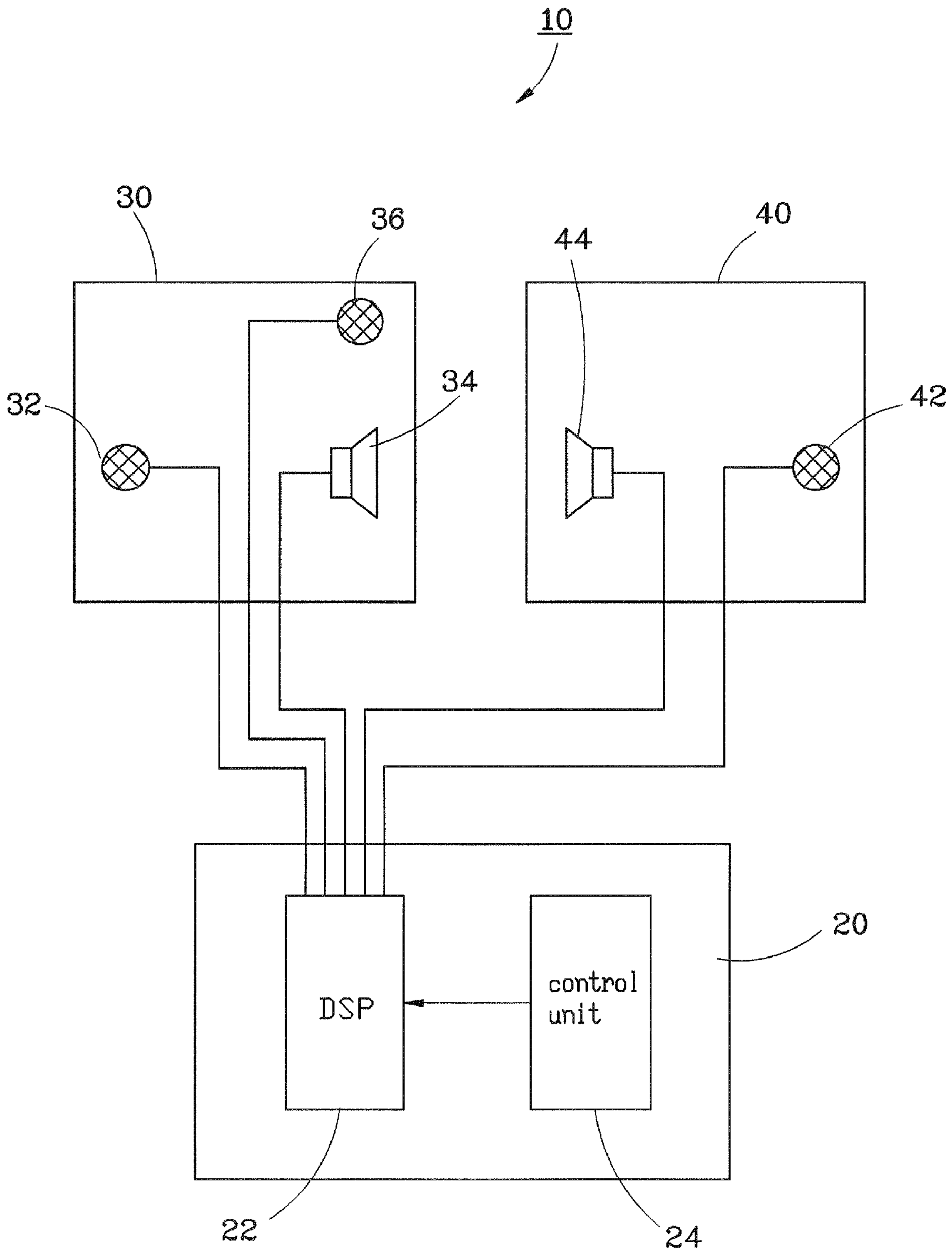
FIG. 2 is a schematic drawing showing the architecture of the earphone set of the present invention.

As shown in FIGS. 1 and 2, an earphone set 10 in accordance with a preferred embodiment of the present invention comprises a main device 20, a first earplug 30, and a second earplug 40.

The main device 20 includes a digital signal processor (DSP) 22, a control unit 24, and a connection line 26. The digital signal processor 22 is adapted for processing electronic signals. The control unit 24 allows the user to operate the main device 20, thereby switching the digital signal processor 21 to, for example, regulate the sound volume. The digital signal processor 22 has at least filtering and amplification functions for processing electronic signals, i.e., the digital signal processor 22 can use a noise cancellation technique to cancel external noises from the received sound signal. The connection line 26 is adapted for connecting the main device 20 to a mobile phone (not shown).

The first earplug 30 comprises an external microphone 32, a speaker 34, and an internal microphone 36. The external microphone 32 is electrically connected to the main device 20, and adapted to convert an external sound wave into an electronic signal and to transmit the electronic signal to the digital signal processor 22 for processing. The speaker 34 is electrically connected to the main device 20, and adapted to receive the processed electronic signal from the digital signal processor 22 and to convert the electronic signal into a sound wave for output into the ear canal of the user. The internal microphone 36 is electrically connected to the main device 20 for receiving the sound wave from the ear canal of the user when the user is talking.

The second earplug 40 comprises an external microphone 42 and a speaker 44. The external microphone 42 is electrically connected to the main device 20, and adapted to convert an external sound wave into an electronic signal and to transmit the electronic signal to the digital signal processor 22 for processing. The speaker 44 is electrically connected to the main device 20, and adapted to receive the processed electronic signal from the digital signal processor 22 and to convert the electronic signal into a sound wave for output into the ear canal of the user.

Figure 3:
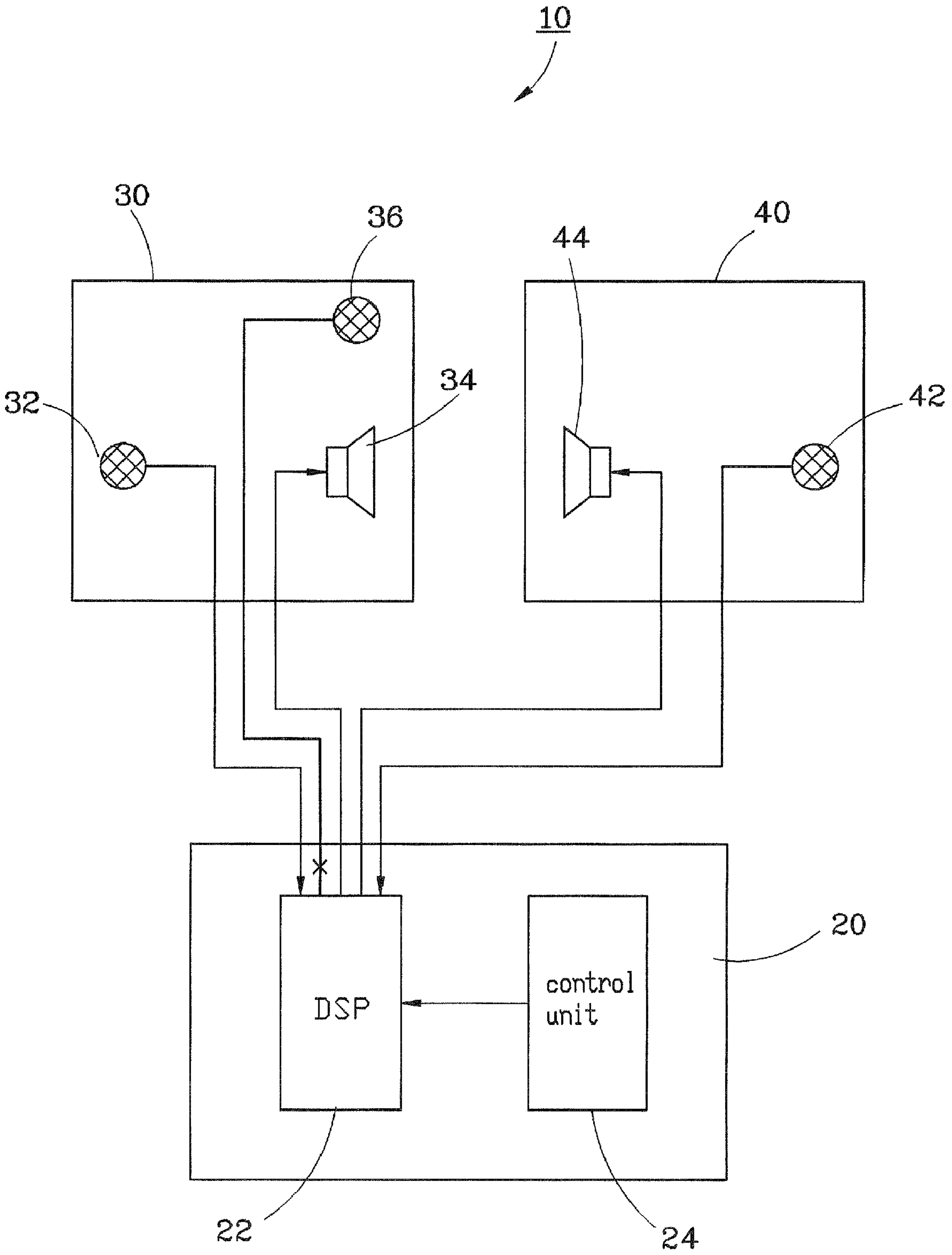
FIG. 3 is a schematic drawing showing the operation of the earphone set under hearing aid mode.

Referring to FIG. 3, when the earphone set 10 is in the hearing-aid mode, the external microphone 32 of the first earplug 30 and the external microphone 42 of the second earplug 40 respectively receive the external sound and convert the external sound into an electronic signal, and then transmit the electronic signal to the digital signal processor 22 for processing and noise cancellation. The digital signal processor 22 then transmits the processed signal to the speakers 34 and 44 that in turn convert the signal into sound for output into the ear canal of the user respectively so that the user can hear quality sound.

Further, in actual practice, the earphone set 10 can be operated to use only the external microphone 32 of the first earplug 30 for receiving the external sound wave and converting it into an electronic signal for processing by the digital signal processor 22, for enabling the processed signal to be further converted into sound by the speaker 34 for output into the ear canal of the user.

Figure 4:
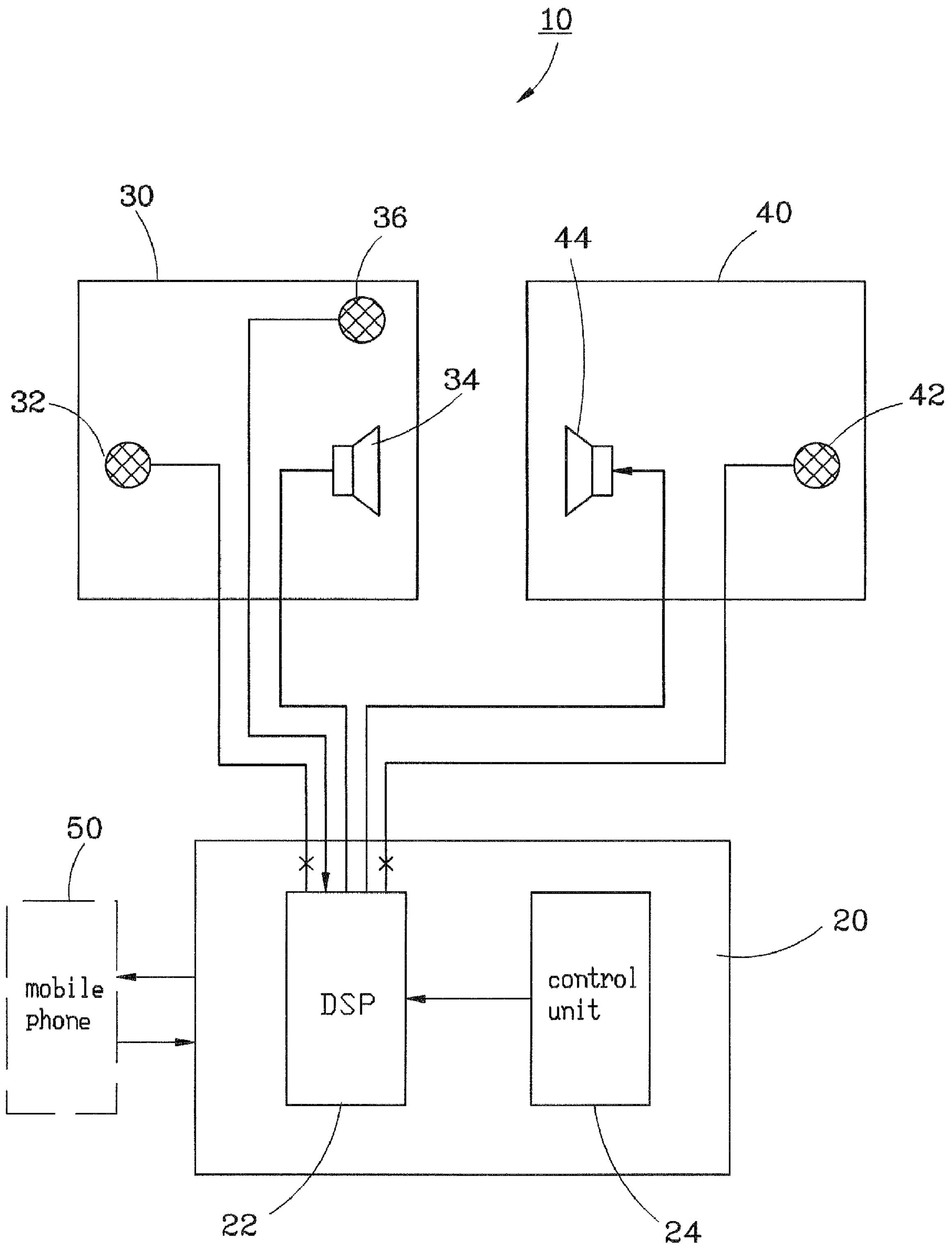
FIG. 4 is a schematic drawing showing the operation of the earphone set under the speak mode.

Referring to FIG. 4, when the earphone set 10 operated with a mobile phone 50, which can operate in the speak mode for receiving a phone call. In this mode, the main device 20 is electrically connected to the mobile phone 50 for two-way conversation. When the user is speaking, the internal microphone 36 of the first earplug 30 receives the sound wave from the ear canal of the user for output through the main device 20 and the mobile phone 50. When the earphone set 10 receives the signal from the mobile phone 50, the digital signal processor 22 of the main device 20 transmits the processed signal to the second earplug 40 for output into the ear canal of the user through the speaker 44. In actual practice, it can be selected to transmit the processed signal from the digital signal processor 22 to the first earplug 30 for output into the ear canal of the user through the speaker 34. By means of the earphone set 10, a hearing-impaired can receive a telephone call conveniently.

Figure 5:
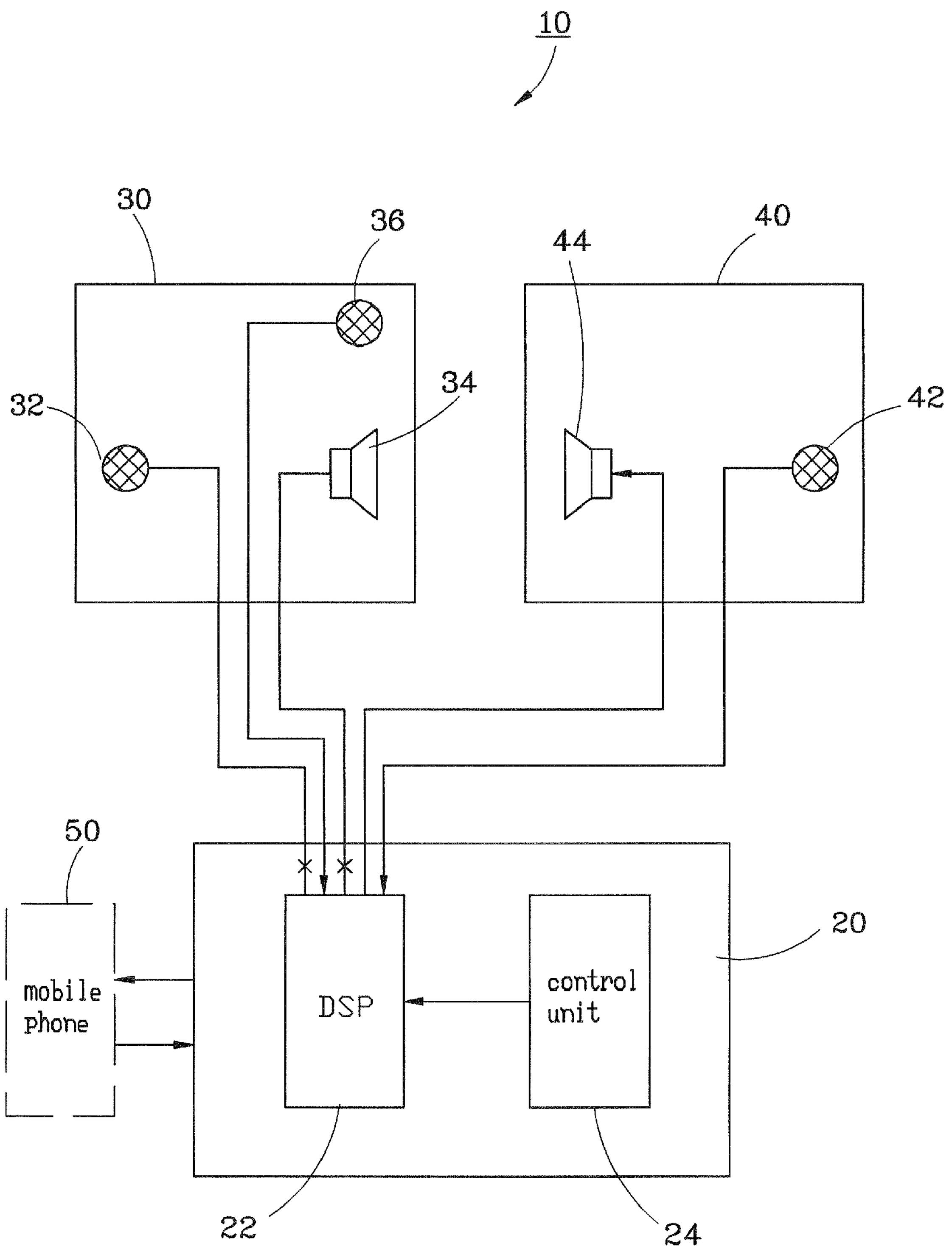
FIG. 5 is a schematic drawing showing the operation of the active noise cancellation of the earphone set under the speak mode.

Referring to FIG. 5, if the external noise level is excessively high, a hearing-impaired can operate the control unit 24 of the main device 20 to perform active noise cancellation (ANC) during the speak mode. The external microphone 42 of the second earplug 40 receives the external sound wave for use as a reference value, and the digital signal process 22 will add an anti-noise sound source in accordance with the spectrum characteristic of the external sound wave. The anti-noise sound source is outputted through the speaker 44 of the second earplug 40. The anti-noise sound source has the same amplitude but opposite phase relative to the external noise, and therefore the anti-noise sound source and the noise offset each other, achieving noise cancellation. Therefore, the earphone set 10 of the present invention can actively cancel external noises, improving sound quality.

Figure 6:
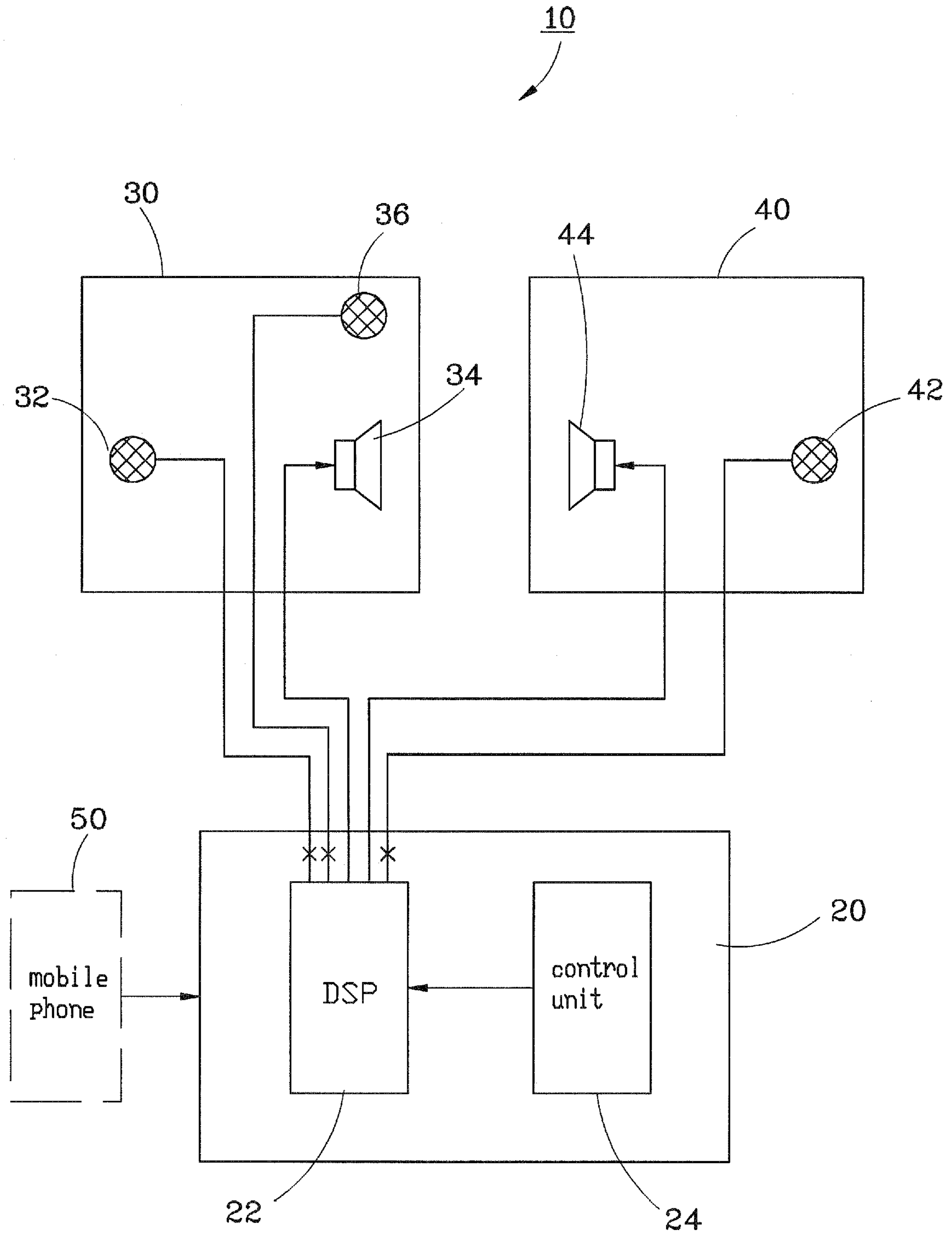
FIG. 6 is a schematic drawing showing the operation of the earphone set under the music-listening mode.

Referring to FIG. 6, when the hearing-impaired uses a mobile phone 50 to listen music, the earphone set 10 is set in the music mode. The music is transmitted from the mobile phone 50 to the main device 20 through a one-way transmission for processing by the digital signal processor 22 of the main device 20 in accordance with the hearing requirement of the hearing-impaired, and the processed electronic signal will be transmitted by the main device 20 to the first earplug 30 and the second earplug 40 for output into the ear canals of the hearing-impaired through the speakers 34 and 44 respectively, and therefore the hearing-impaired can listen to the must in the stereo mode.

Figure 7:
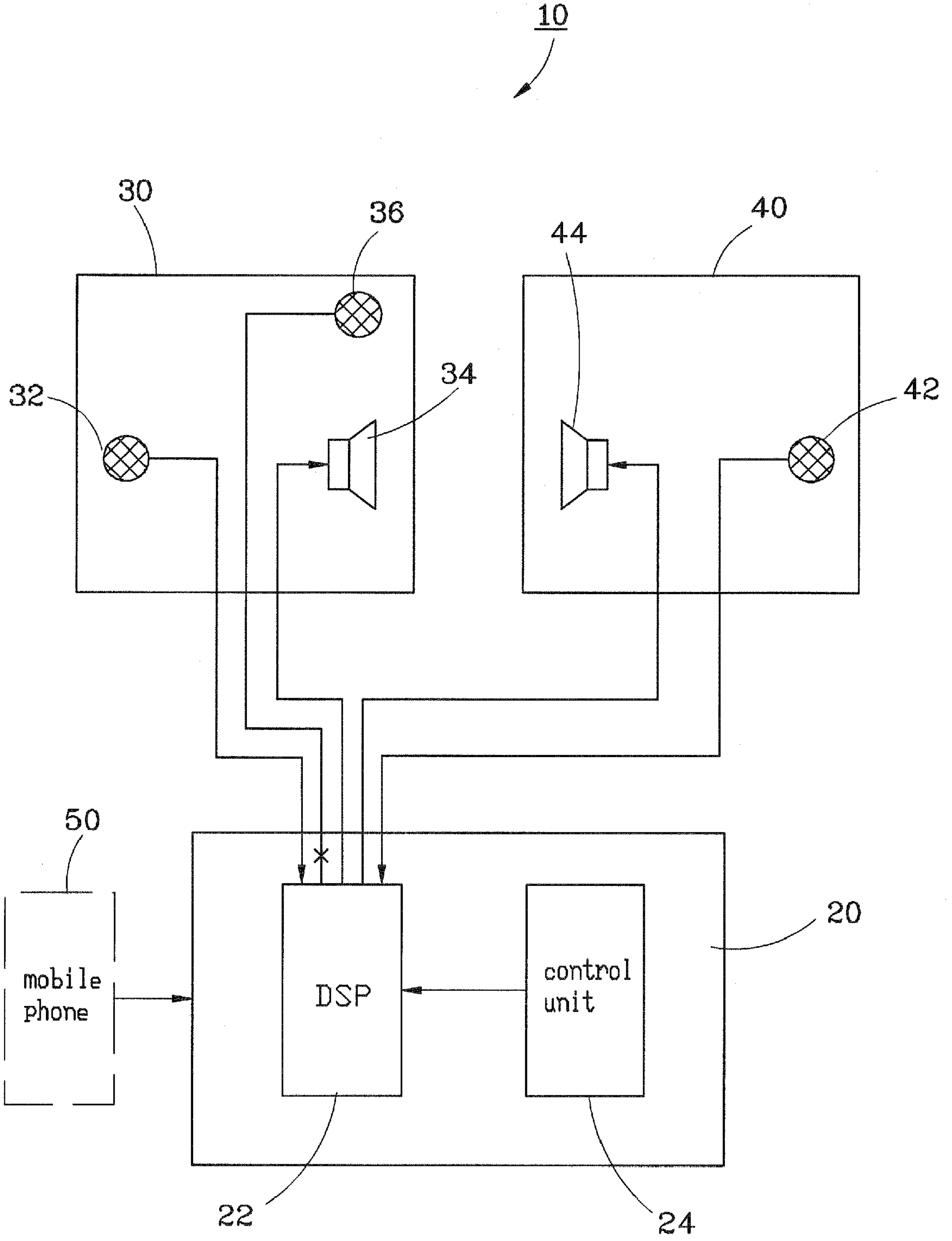
FIG. 7 is a schematic drawing showing the operation of the active noise cancellation of the earphone set under the music-listening mode.

Referring to FIG. 7, if the hearing-impaired feels that the external noise level is excessively high and he (she) cannot hear the sound clearly during the music mode, the hearing-impaired can operate the control unit 24 of the main device 20 to perform active noise cancellation (ANC). At this time, the external microphone 32 of the first earplug 30 and the external microphone 42 of the second earplug 40 receive the external sound waves for use as a reference value, and the digital signal process 22 will add an anti-noise sound source in accordance with the spectrum characteristic of the external sound waves. Therefore, the earphone set 10 of the present invention can actively cancel external noises, improving sound quality.

In conclusion, the invention provides an earphone set for a hearing-impaired with a hearing aid function as well as an earphone function, eliminating the problem that an earphone set cannot be used when a hearing aid is issued, and bringing convenience to a hearing-impaired. Further, the internal microphone receives the sound wave transmitted from the ear canal of the hearing-impaired for converting into an electronic signal for output through a mobile phone as the hearing-impaired is speaking. Further, the invention uses noise cancellation technology to cancel external noises, improving sound quality.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An earphone set, comprising:

a main device having a digital signal processor;

a first earplug having a first external microphone, an internal microphone and a first speaker respectively and electrically connected to the digital signal processor;

a second earplug having a second external microphone and a second speaker electrically connected to the digital signal processor; and wherein, when the earphone set operates in a hearing-aid mode, the first external microphone converts an external sound wave into a first electronic signal and then transmits the first electronic signal to the digital signal processor for processing, and the first speaker converts the first electronic signal processed by the digital signal processor into a sound wave for output into an ear canal of a user;

wherein when the earphone set communicates with a mobile phone and operates in a speak mode, the internal microphone receives a sound wave from the ear canal and converts the received sound wave into a second electronic signal for transmission to the mobile phone, the second speaker receives a third electronic signal transmitted from the mobile phone and processed by the digital signal processor and then converts the third electronic signal into a sound wave for output into another ear canal of the user, and a second external microphone receives the external sound wave for use as a reference value for enabling the digital signal processor to produce an anti-noise sound source for output through the second speaker to cancel noises.

2. The earphone set as claimed in claim 1, wherein the digital signal processor has at least one of the functions of filtering and amplification.

3. The earphone set as claimed in claim 1, wherein the main device further comprises a control unit electrically connected to the digital signal processor for switching of functions of the digital signal processor.

4. The earphone set as claimed in claim 1, wherein the anti-noise sound source has the same amplitude of the external sound wave received by the second external microphone in an opposite phase.

5. The earphone set as claimed in claim 1, which is communicated to the mobile phone for enabling the first speaker to convert a forth electronic signal transmitted from the mobile phone and processed by the digital signal processor into a sound wave for output into the ear canal of the user.

6. The earphone set as claimed in claim 5, wherein the forth electronic signal transmitted from the mobile phone is a sound signal or a music signal.

* * * * *